United States Patent [19]
Nallakrishnan

[11] Patent Number: 5,620,453
[45] Date of Patent: Apr. 15, 1997

[54] SURGICAL KNIFE WITH RETRACTABLE BLADE AND DEPTH OF CUT CONTROL

[76] Inventor: Ravi Nallakrishnan, 26 Plaza Dr., Westmont, Ill. 60559

[21] Appl. No.: 372,849

[22] Filed: Jan. 13, 1995

Related U.S. Application Data

[63] Continuation of Ser. No. 147,847, Nov. 5, 1993, abandoned.
[51] Int. Cl.$^6$ .................................................. A61B 17/32
[52] U.S. Cl. ................... 606/166; 606/167; 30/293; 30/335
[58] Field of Search .................... 606/166, 167, 606/170, 172; 30/164.92, 164.93, 164.95, 293, 335

[56] References Cited

U.S. PATENT DOCUMENTS

| | | | |
|---|---|---|---|
| 4,499,898 | 2/1985 | Knepshield et al. | 606/166 |
| 4,898,170 | 2/1990 | Hofmann et al. | 606/166 |

FOREIGN PATENT DOCUMENTS

| | | | |
|---|---|---|---|
| 2113550 | 8/1983 | United Kingdom | 606/166 |
| 8705799 | 10/1987 | WIPO | 606/166 |

*Primary Examiner*—Michael Powell Buiz
*Assistant Examiner*—William Lewis
*Attorney, Agent, or Firm*—Jerry A. Schulman

[57] ABSTRACT

A surgical knife for use in ophthalmic surgery includes a bladeholder assembly holding a surgical cutting blade, with the bladeholder assembly sliding into and out of a hollow knife handle, and a plunger mechanism manually operable to move said bladeholder assembly to a position where the cutting blade is exposed and usable for surgery. The knife also includes a depth of cut control which sets the depth to which the blade is used to make an ocular incision and which allows the plunger mechanism to extend and retract the bladeholder assembly without changing the depth of cut. A modified micrometer scale allows the depth of cut to be conveniently changed by a given distance without recalculating the cutting depth.

3 Claims, 3 Drawing Sheets

SURGICAL KNIFE WITH RETRACTABLE BLADE AND DEPTH OF CUT CONTROL

This is a continuation of application Ser. No. 08/147,847, filed 05 Nov. 1993, now abandoned.

This invention relates generally to surgical knives and, more particularly, to knives with controls for setting and changing the cutting depth of the blade during surgery and which allow the blade to be retracted into the knife handle without altering the depth of cut.

BACKGROUND OF THE INVENTION

Ophthalmic surgeons work within a very small operating field upon organs whose tissues are complex and delicate. Cuts made during surgery must be precise as to length, direction and depth, requiring surgical knives of unsurpassed sharpness and maneuverability.

During surgery, there are times when particular knives, set to particular cutting depths, must be used. Often, it is necessary to change the depth of cut during surgery. Depending upon the method originally used to set the original depth of cut, it may be necessary to interrupt the surgery to make the needed changes. Where the depth of cut is simply to be increased by a selected amount, it is necessary for the surgeon to then calculate the new depth setting by adding the additional depth to the original setting and then resetting the knife to the new setting.

Surgical knives with micrometer settings are well-known in the art. U.K. Patent 2 113 550 (Kemp) typifies a surgical knife having a cutting blade which is extendible from the body of the knife by rotating the knife handle with respect to the knife body. U.S. Pat. No. 4,898,170 (Hofmann, et al.) teaches and describes a knife which incorporates a micrometer mechanism coupled to an offset head which holds a surgical cutting blade. U.S. Pat. No. 4,516,575 (Gerhard, et al.) teaches and describes a surgical knife with a micrometer mechanism used to measure the advance of the cutting blade, with provision to recalibrate the micrometer to accommodate variations in blade or blade holder configuration. U.S. Pat. No. 4,499,898 (Knepshield, et al.) teaches and describes a surgical blade holder having a micrometer-like mechanism to advance a cutting blade and a measuring scale usable to determine the depth of cut as the blade is advanced.

The Kemp (U.K.), Hofmann, et al., Gerhard, et al. and Knepshield, et al. references all show surgical knives which may be set to cut to a predetermined depth by advancing the cutting blade beyond a "foot" formed or positioned at one end of the knife. Once the cutting depth is set, however, the blade must be left exposed, as the only provision for moving the blade into the handle is to retract the blade past the foot.

Gerhard, et al. teach and describe a method for zeroing the micrometer scale when the leading edge of the cutting blade is aligned with the foot.

The distance the cutting blade extends from the knife holder is often set prior to surgery, and while the knife is not being used, it is desirable to protect the cutting blade from accidental contact with the hands or clothing of operating room personnel, and from damage that may occur from being dropped or contacted by other instruments. Loss of such a knife due to accident often means that the surgical procedure must be halted until another knife can be obtained and set for the same cutting depth as the original knife.

In U.S. Pat. No. 3,176,395, there is described a photoengraver's knife having a blade which can be fully withdrawn into the hollow handle of the knife, to protect both the blade and users of the knife between cutting operations.

The need then exists for an ophthalmic surgical knife which allows the depth of cut to be preset and thereafter to be changed during surgery without requiring an interruption to the surgical procedures.

The need also exists for a system of resetting the depth of cut which allows the surgeon conveniently to increase the depth of the cut by a chosen dimension without calculating and setting a new cutting depth.

The need also exists for a surgical knife with the capability of allowing the depth of cut to be set and, thereafter, allowing the blade to be covered or protected in a manner which does not affect the depth setting.

BRIEF DESCRIPTION OF THE INVENTION

A surgical knife has a plunger which fits telescopically within one end of a hollow handle or housing. The plunger has a knob used manually to extend the plunger into and out of the handle from a first, open end of the handle. The handle includes a hollow blade sheath terminating in a footplate beyond which the blade is extended to set the depth of cut.

At the other end of the handle, a blade holder assembly is mounted, sized to allow the blade holder and, thereby, the cutting blade, to be fully retracted within the sheath when the plunger is extended outward from the handle. The plunger includes a jam bearing which prevents the blade from being forced back into the sheath during surgery, but which allows the blade to be fully retracted within the sheath by pulling the plunger.

The handle includes a micrometer mechanism which allows the depth of cut to be set by advancing the blade holder and, thereby the blade,beyond the foot by a distance equal to the depth of the cut. A modified scale included on the micrometer mechanism allows the user to change the blade exposure and, thereby, the depth of cut, by a selected distance without having to calculate the new depth of cut and thereafter to use the main micrometer scale to reset the depth.

BRIEF DESCRIPTION OF THE DRAWINGS

These and other aspects of the present invention will become more apparent upon a consideration of the accompanying drawings, in which.

DETAILED DESCRIPTION OF THE DRAWINGS

Figure 1:
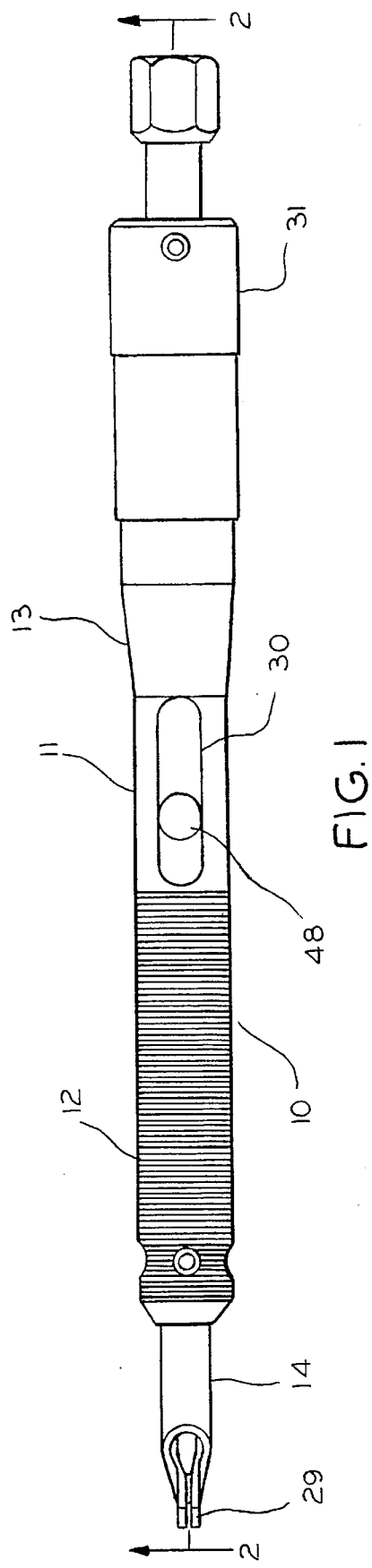
FIG. 1 is a side elevational view of a preferred embodiment of the present invention showing the blade holder extended from the knife handle.

Referring now to FIG. 1, the numeral 10 indicates generally a surgical knife of the type herein generally described. Knife 10 has a hollow, generally cylindrical housing or handle 11 with a handgrip portion 12 having a ribbed or otherwise textured gripping surface.

As seen in FIG. 1, handle 11 is not uniform in cross-sectional shape, but has an enlarged "waist" 13 tapering radially outward to a diameter larger than that of handle portion 12. Handle 11 includes a hollow cylindrical tube or sheath 14 attached to one end of handle 11.

Figure 4:
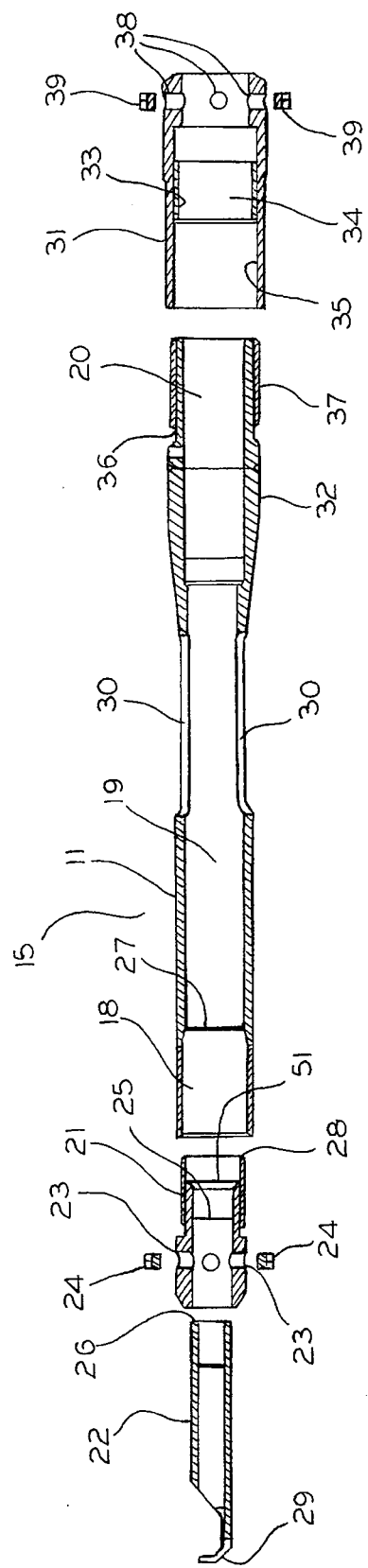
FIG. 4 is an exploded sectional view of the handle assembly.
Figure 5:
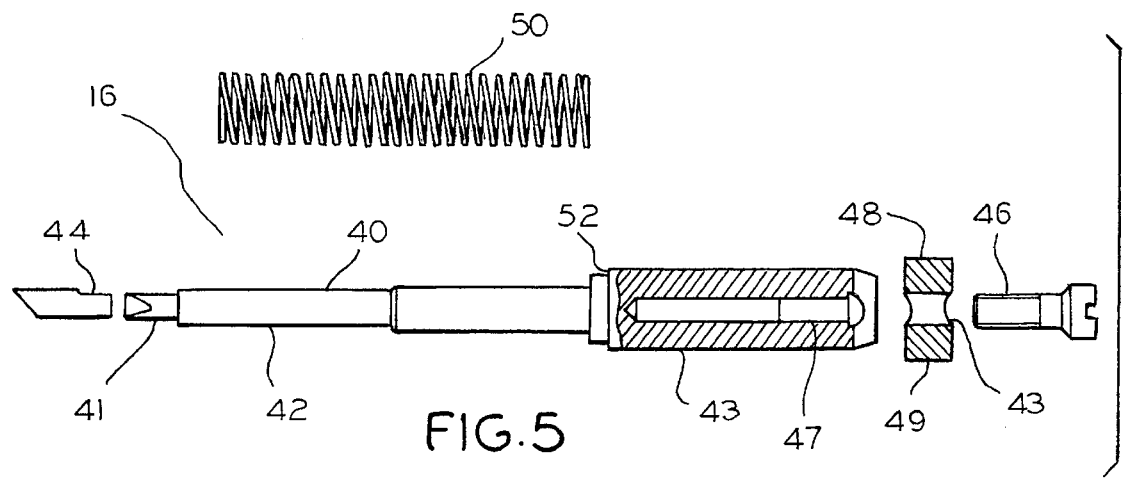
FIG. 5 is an exploded sectional view of the blade holder assembly.
Figure 6:
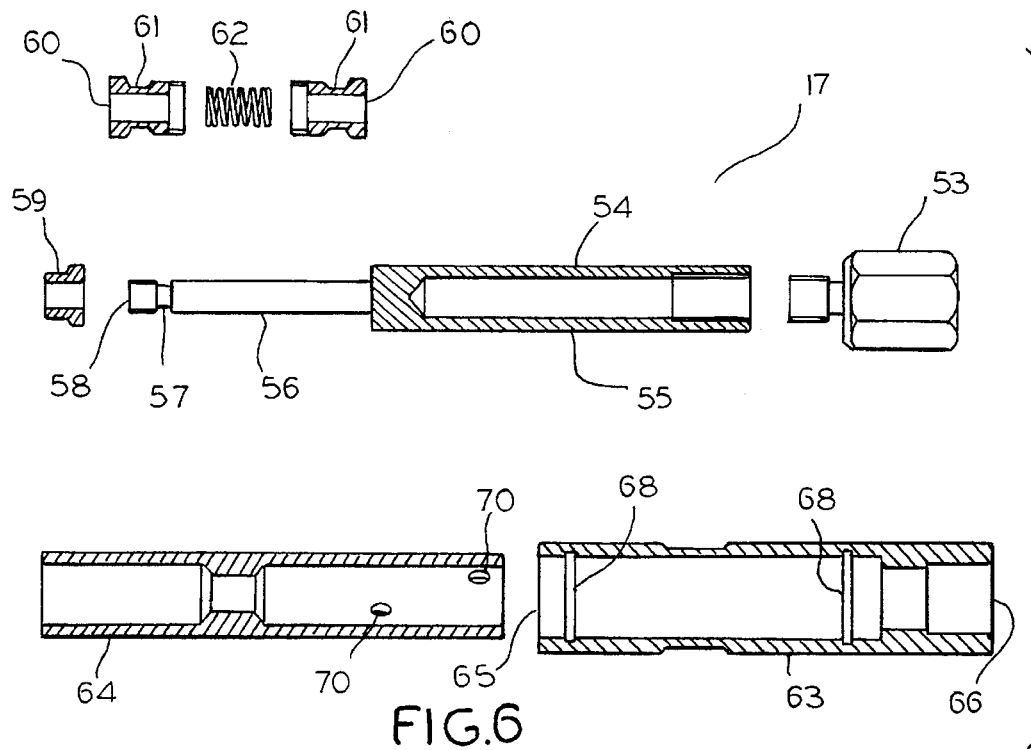
FIG. 6 is an exploded sectional view of the plunger assembly.

Referring now to FIGS. 3, 4, 5 and 6, it can be seen that a plunger-actuated mechanism 15 extends throughout the length of hollow handle 11, composed generally of three separate assemblies: a handle assembly 15 (FIG. 4), a bladeholder assembly 16 (FIG. 5) and a plunger assembly 17 (FIG. 6).

Referring to FIG. 4, handle assembly 15 includes hollow handle 11, having a front chamber 18, a central chamber 19 and a rear chamber 20. In a preferred embodiment of the invention, the open end of handle 11 is closed off by inserting a hollow handle plug 21 into front chamber 18. A hollow sheath 22 is inserted into plug 21 and is secured in place by a series of set screws 24 screwed into threaded apertures 23, spaced regularly about the outer periphery of plug 21. Plug 21 has a land formed therewithin against which rear edge 26 of sheath 22 is abutted when sheath 22 is fully inserted into plug 21. In similar fashion, land 27 is formed within handle 11 against which a rear edge 28 of plug 21 is abutted when plug 21 is fully inserted into chamber 18 of handle 11.

In an alternate embodiment, the physical features of plug 21 are incorporated as an integral part of the structure of handle 11.

Referring to FIGS. 1 and 4, a footplate 29 is formed at the forward end of sheath 22. The extent to which a cutting blade extends beyond the footplate 22 determines the depth of cut in a manner to be described below. The same figures illustrate a pair of guide slots 30, formed in handle 11 diametrically opposed to and parallel to each other, and parallel to the axis of handle 11.

FIGS. 1 and 4 also show a micrometer thimble 31 which is threadably and rotatably assembled to rear end 32 of handle 11, that end opposite to that at which sheath 22 is attached. Thimble 31 has screw threads 33 formed within chamber 34 on interior wall 35. Threads 37 are likewise formed on an outside rear handle surface 36, and engage threads 33 to enable thimble 31 to be threaded onto and, thereby travel axially along handle 11 when rotated. Completing a description of thimble 31, a series of tapped or threaded apertures 38 are formed about the periphery of thimble 31, with a series of set screws 39 screwed into apertures 38.

Figure 2:
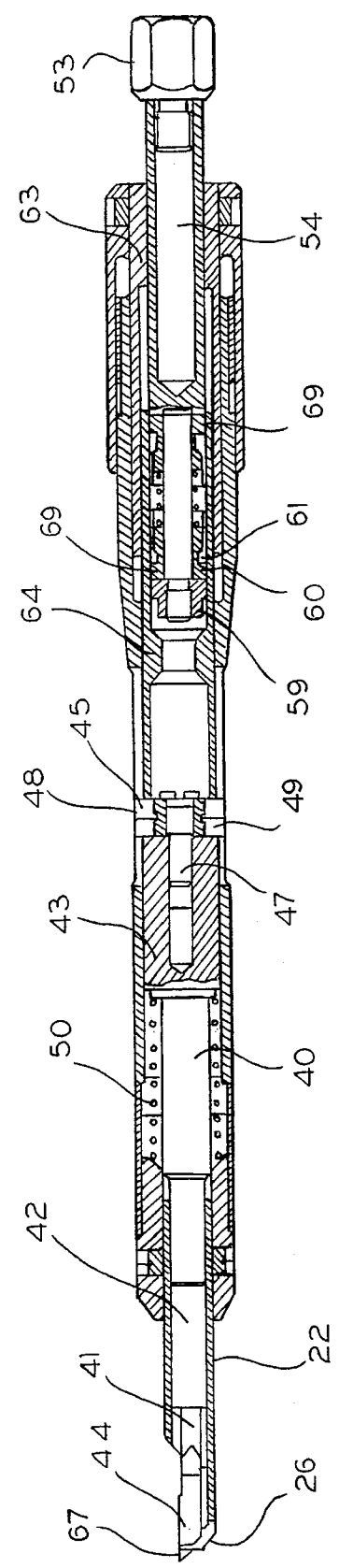
FIG. 2 is a view along 2—2 of FIG. 1, showing the embodiment of FIG. 1 in full section.

Referring now to FIG. 5, the constituent parts of bladeholder assembly 16 include bladeholder plunger 40 which, at one end thereof, has a bladeholder 41, and intermediate barrel segment 42 and a rearmost mounting block 43. Bladeholder 41 is built to grip and hold a surgical cutting blade 44, and bladeholder plunger 40 is sized and shaped to fit within handle 11 where, as shown in FIG. 2, bladeholder plunger 40 is slidably received within chambers 18 and 19, with bladeholder 41 and, thereby, blade 44 slidably received within sheath 22. The direction and extent of movement of bladeholder plunger 40 within handle 11 is determined by a guide block 45, assembled to mounting block 43 by a screw 46 threaded into a tapped aperture 47. When assembled within handle 11, each of the "ears" 48 and 49 of guide block 45 protrude through one guide slot 30. In this fashion, the length of travel of bladeholder plunger 40 is limited by the length of slots 30. In addition, the movement of guide block ears 48 in slots 30 prevents mounting block 43 from rotating, keeping blade 44 straight within sheath 22 and footplate 29 during use.

As seen in FIGS. 2 and 5, a return spring 50 is used to bias plunger 40 to move in a rearward direction and to oppose movement in a forward position. In other words, spring 50 normally moves plunger 40 and, thereby, blade 44 in a rearward direction, drawing blade 44 into sheath 22. As seen in FIG. 2, when knife 10 is assembled, one end of spring 50 abuts plug shoulder 51 and the remaining end abuts mounting block shoulder 52.

Referring now to FIG. 6 and plunger assembly 17, it can be seen that plunger knob 53 is attached to knob shaft 54. Shaft 54 has a first, hollow shaft section 55 and a second, solid shaft section 56 smaller in diameter than section 55. An annular groove 57 extends circumferentially about shaft section 55 proximate the tip 58 of the shaft section. A fastener 59, such as a cap nut or "high-hat" is snap- or press-fit to shaft 56 at tip 58, fitting into groove 57.

Also seen in FIG. 6 are a pair of conuses 60, each having a circumferentially-extending groove 61, and spacer coil spring 62. When assembled, each conus is slipped onto shaft 56, with spring 62 disposed therebetween. As described more fully hereinbelow, a number of ball bearings are nested in grooves 61 when each conus 60 is assembled to knife 10.

Also included in plunger assembly 17 are plunger cylinder 63 and plunger sleeve 64, which fit together telescopically, with sleeve 64 fitting within cylinder 63. When assembled, sleeve 64 slides into cylinder 63 through cylinder front end 65, and knob shaft 54, with fastener 59, conuses 60, ball bearings 61, and spring 62 installed thereon, slides into cylinder 63 through cylinder rear end 66.

When installed into handle 11, plunger assembly 17 is inserted into rear chamber 20. Micrometer thimble 31 is then threaded onto rear handle end 32, and screws 39 are tightened to assemble thimble 31 to cylinder 63. Cylinder 63 thus moves in an axial, or fore-and-aft direction within handle 11 as micrometer thimble 31 is rotated. Knob shaft 54 is attached to sleeve 64 by, for example, a pin extending through both sleeve 64 and hollow shaft section 55 such that when knob 53 is pushed, shaft 54 and sleeve 64 move toward the front end of handle 11.

Figure 3:
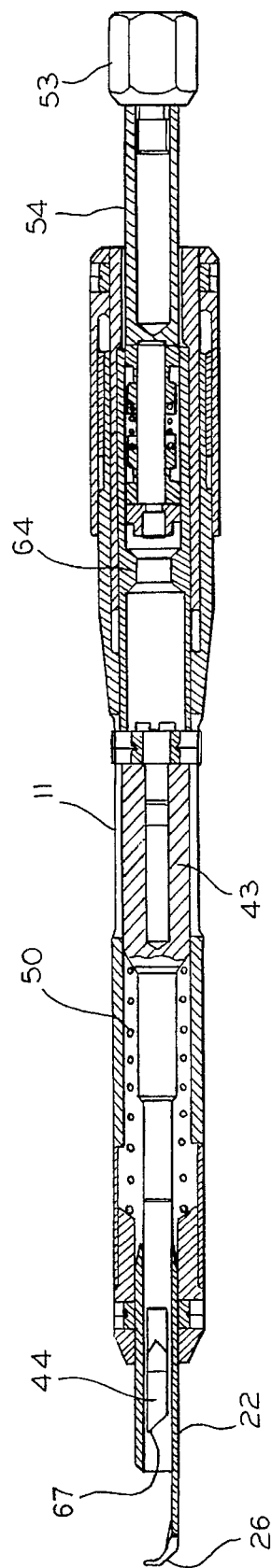
FIG. 3 is a modified view of FIG. 2 showing the blade holder withdrawn into the knife handle.

Referring to FIGS. 2 and 3, showing knife 10 fully assembled, the operating features of knife 10 may now be described.

FIG. 2 shows knife 10 with blade 44 extended in a position to make a cut or incision. Tip 67 of blade 44 is extended beyond footplate 29 to provide a cutting edge. The distance by which tip 67 extends past footplate 29 is the depth of cut because footplate 29 rests upon the eye when knife 10 is used during surgery. In this extended position, knob 53 has been pushed to advance sleeve 64 forward. As described above, spring 50 urges mounting block 43 rearward in handle 11 until, as shown in FIG. 2, mounting block 43 comes into contact with and abuts sleeve 64. The movement of guide block ears 48 and 49 in guide slots 30 keeps the fore-and-aft motion of mounting block 43 straight and also keeps block 43 and, thereby, bladeholder 41 from rotating or twisting during cutting.

To change the depth of cut, micrometer thimble 31 is rotated which causes it to travel axially in a fore-and-aft direction along handle 11. As thimble 31 moves, it also moves plunger cylinder 63 as well which, in turn, advances sleeve 64 and, thereby, bladeholder plunger 40 to change the position of blade tip 67. As seen in FIG. 3, when blade tip 67 is to be withdrawn or retracted into handle 11, plunger knob 53 is pulled to move knob shaft 54 and, thereby, sleeve 64 rearward. As spring 50 moves toward its relaxed or unstressed position, it pushes bladeholder plunger 40 rearward, to follow the travel of sleeve 64, drawing bladeholder 41 and blade tip 67 into sheath 22.

It is a feature of the present invention that once the cutting depth is set using micrometer thimble 31, blade tip 67 can be retracted and extended without changing the cutting depth. To accomplish this, each time sleeve 64 is advanced through cylinder 63 by plunger shaft 54, sleeve 64 is stopped and secured at the same point within cylinder 63. In this manner, the total, effective movement of cylinder 63 and sleeve 64 through handle 11 is constant. Cylinder 63 and sleeve 64 move as a unit when micrometer thimble 31 is adjusted, thus changing the position of cylinder 63 and sleeve 64 relative to handle 11. Because sheath 22 and, thereby, footplate 29 are fixed in relation to handle 11, and because the travel of cylinder 63 and sleeve 64 is always the same distance, the final, extended position of blade 44 is affected only by the rotation of thimble 31. In other words, the travel of the entire plunger assembly through handle 11 is a constant distance, with thimble 31 adjusting the starting point of the travel of the plunger.

In a preferred embodiment of the present invention, cylinder 63 has circumferentially-extending front and rear grooves 68 formed on the interior surface thereof, and sleeve 64 has locking apertures 70 formed therethrough. When sleeve 64 is advanced with respect to cylinder 63, one of the ball bearings 69 disposed within conus groove 61 engages the forwardmost groove 68, holding sleeve 64 in fixed relationship to cylinder 63. The shape of groove 69 helps to hold conus 68 and, thereby, sleeve 64 in place against force exerted by pressure on blade 44 during surgery. Sufficient force is exerted when knob 53 is pulled to disengage bearing 69 from groove 68 to retract blade tip 67 into sheath 22. Thus, the force with which bearing 69 engages frontmost groove 68 keeps blade tip 67 extended during cutting, helping to prevent accidental retraction of the blade into sheath 22 during use.

Figure 7:
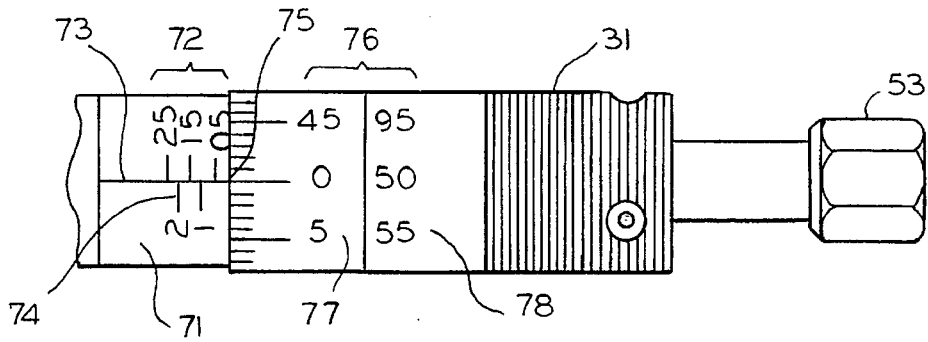
FIG. 7 is a partial view of that portion of the handle assembly of FIG. 1 showing the modified micrometer scale.

Referring now to FIG. 7, details are shown of the gravings on micrometer thimble 31 and on the exterior rear surface 71 of handle 11. Handle marking scale 72 is shown in a conventional and well-known configuration for micrometers. A base line 73 extends axially along surface 71, intersected at right angles by a series of regularly-spaced dimension lines 74. In this example, the dimension lines 74 of scale 72 are marked in 0.5 mm. intervals beginning at zero and going up to 2.5. As micrometer thimble 31 is rotated, thimble edge 75 moves into alignment with various lines on scale 74. A secondary scale 76 is formed on thimble 31, marked in regular intervals about the circumference of thimble 31, with the scale lines extending in an axial direction. In the embodiment herein shown, scale 76 is marked off in 50 equal increments and are numbered on two numeric scales, depth scale 77 and increment scale 78.

Depth scale 77 is numbered from zero to 49, while increment scale 78 is numbered from 50 to 99. In a preferred embodiment of the present invention, one full revolution of micrometer thimble 31 increases the depth of cut by 0.5 mm. Thus, when the zero on scale 77 is aligned with base line 73, edge 75 is aligned with one of the dimension lines 74. For example, in FIG. 7, the zero on scale 77 is aligned with base line 73 and edge 75 is aligned with the zero on micrometer scale 72, meaning that the depth of cut is zero. If thimble 31 is now rotated to advance blade 44, and is rotated one full revolution, when the zero on scale 77 aligns with base line 73, edge 75 will align with micrometer scale marking "0.5", meaning that the depth of cut has been set to 0.5 mm.

Interpolating readings on scale 72 is done by reading the number on scale 77 that is aligned with base line 73 and then adding that number to the lower of the scale numbers on scale 72 between which edge 75 is positioned. For example, if edge 75 is resting between the "1.0" and "1.5" markings on scale 72, and the number "35" on scale 77 aligns with base line 73, the depth of cut is 0.135 mm.

Often during surgery, it is necessary to change the depth of cut by a selected amount, rather than to a specific dimension. Scales 77 and 78 facilitate this task. As an example, if the number "15" is aligned with base line 73, and the surgeon wishes to increase the depth of cut by 0.25 mm., the surgeon need only add 25 to the scale reading of "15" and rotate thimble 31 until the number "40" aligns with base line 73. If the surgeon wishes to increase the depth of cut by 0.55 mm., the number 35 is added to the scale reading of "15" and thimble 31 is rotated to align the resulting number "70" found on scale 78, with base line 73. To decrease the depth of cut, the same procedure is followed, with the decrease being subtracted from the scale reading and thimble 31 being rotated to withdraw blade 44 into knife handle 11.

Footplate 29 and handle 11 are configured such that when knife 10 is assembled and thimble 31 is set to the zero marking on base line 73, blade tip 67 is at a zero depth of cut. If desired, other, well-known methods of zeroing or calibrating micrometer thimble 31 may also be employed.

While the foregoing has described the present invention in terms of preferred embodiments thereof, such description is not intended to limit the scope of the invention. It is expected that others, skilled in the art, will perceive variations which, while differing from the foregoing, do not depart from the spirit and scope of the invention as herein described and claimed.

What is claimed is:

1. A surgical knife, said knife comprising:
   a substantially straight, hollow, generally cylindrical handle terminating in first and second ends and having a central, axially-extending passageway;
   a plunger assembly positioned within and axially moveable along said passageway to an extended position and a retracted position;
   a blade holder assembly to which a surgical cutting blade is mounted,
   said blade holder assembly positioned within said passageway,
   said blade holder assembly axially moveable along said passageway responsive to the movement of said plunger assembly to extend said cutting blade from said first knife handle end and to retract said cutting blade into said knife handle;
   a footplate attached to said first knife handle end;
   means for setting a depth of cut of said cutting blade; and
   means to retain said blade holder assembly in said extended position,
   said retaining means includes means formed on said plunger assembly for engaging mating means formed on an interior surface of said knife handle.

2. A surgical knife, said knife comprising:
   a hollow, generally cylindrical handle terminating in first and second ends and having a central, axially-extending passageway;
   a blade holder assembly axially moveable along said passageway to extend said cutting blade from said first handle end and to retract said cutting blade into said handle;

a surgical cutting blade mounted to said blade holder assembly, a footplate attached to said first handle end; and means for setting a depth of cut of said cutting blade by extending or retracting said cutting blade to a desired distance beyond said footplate, said depth setting means including a micrometer thimble in threaded engagement with the exterior surface of said handle at said second handle end, whereby rotation of said thimble causes said cutting blade assembly to move in an axial position within and relative to said handle;

said depth setting means further including a base line scribed on said knife handle, said base line extending in an axial position along said knife handle; and a scale scribed on said thimble, said thimble scale including a series of scale lines regularly spaced about the periphery of said thimble and extending in said axial direction, said thimble scale lines arrayed to bring successive of said lines into alignment with said base line as said thimble is rotated, said scale lines numbered about said thimble periphery to form a numerical depth scale and a numerical increment scale parallel one to another, said depth scale being numbered from 0 to 50 and said increment scale being numbered in identically-spaced increments from 50 to 100, with the numbers 0 on the depth scale and 50 on the increment scale coinciding.

3. A surgical knife, said knife comprising:

a substantially straight, hollow, generally cylindrical handle terminating in first and second ends and having a central, axially-extending passageway;

a plunger assembly positioned within and axially moveable along said passageway to an extended position and a retracted position;

a blade holder assembly to which a surgical cutting blade is mounted, said blade holder assembly positioned within said passageway, said blade holder assembly axially moveable along said passageway responsive to the movement of said plunger assembly to extend said cutting blade from said first knife handle end and to retract said cutting blade into said knife handle;

a footplate attached to said first knife handle end;

means for setting a depth of cut of said cutting blade by extending or retracting said cutting blade to a desired distance beyond said footplate, said depth setting means further including a base line scribed on said knife handle, said base line extending in an axial position along said knife handle; and a scale scribed on said thimble, said thimble scale including a series of scale lines regularly spaced about the periphery of said thimble and extending in said axial direction, said thimble scale lines arrayed to bring successive of said lines into alignment with said base line as said thimble is rotated, said scale lines numbered about said thimble periphery to form a numerical depth scale and a numerical increment scale parallel one to another, said depth scale being numbered from 0 to 50 and said increment scale being numbered in identically-spaced increments from 50 to 100, with the numbers 0 on the depth scale and 50 on the increment scale coinciding; and means to retain said blade holder assembly in said extended position, said retaining means includes means formed on said plunger assembly for engaging mating means formed on an interior surface of said knife handle.

* * * * *